US012616432B2

(12) United States Patent
Gennari

(10) Patent No.: US 12,616,432 B2
(45) Date of Patent: May 5, 2026

(54) COMPRESSION DEVICE FOR BREAST EXAMS AND DIAGNOSTIC APPARATUS FOR BREAST EXAMS

(71) Applicant: SINCRONIS MEDICAL SRL, Cinisello Balsamo (IT)

(72) Inventor: Danilo Gennari, Cinisello Balsamo (IT)

(73) Assignee: NOVAURA SRL, Milan (IT)

( * ) Notice: Subject to any disclaimer, the term of this patent is extended or adjusted under 35 U.S.C. 154(b) by 153 days.

(21) Appl. No.: 18/263,834

(22) PCT Filed: Feb. 9, 2022

(86) PCT No.: PCT/IB2022/051145
§ 371 (c)(1),
(2) Date: Aug. 1, 2023

(87) PCT Pub. No.: WO2022/175785
PCT Pub. Date: Aug. 25, 2022

(65) Prior Publication Data
US 2024/0115223 A1      Apr. 11, 2024

(30) Foreign Application Priority Data
Feb. 17, 2021      (IT) ........................ 102021000003593

(51) Int. Cl.
A61B 6/50          (2024.01)
A61B 6/04          (2006.01)
(52) U.S. Cl.
CPC ............ A61B 6/502 (2013.01); A61B 6/0414 (2013.01)

(58) Field of Classification Search
CPC ......... A61B 6/502; A61B 6/50; A61B 6/0414; A61B 6/0421; A61B 6/0407; A61B 5/708;
(Continued)

(56) References Cited

U.S. PATENT DOCUMENTS 6,587,578 B2      7/2003   Godik
2007/0223652 A1   9/2007   Galkin
(Continued)

FOREIGN PATENT DOCUMENTS

DE      2335576 A1      1/1975
FR      2702059 A1      9/1994
WO      9842248 A2      10/1998

OTHER PUBLICATIONS

International Search Report dated May 20, 2022 from counterpart PCT App No. PCT/IB2022/051145.

*Primary Examiner* — Don K Wong
(74) *Attorney, Agent, or Firm* — SHUTTLEWORTH & INGERSOLL, PLC; Timothy J. Klima

(57) ABSTRACT
A breast examination compression device, including a support element defining a flat surface made at least in part of material transparent to light and configured to come into contact with a lower area of the breast; a substantially box-like body made at least in part of transparent material and including at least one elastic and deformable wall configured to compress an upper area of the breast, said elastic wall being opposite the flat surface; and orientation means of the box-like body for moving the body itself with respect to the support element and as a function of the dimensions and shape of the breast.

20 Claims, 4 Drawing Sheets

(58)  Field of Classification Search
      CPC ........... A61B 5/70; A61B 5/704; A61B 8/403;
                  A61B 5/4312; A61B 5/0091; A61B
                  2018/00333; A61B 2017/3407
      See application file for complete search history.

(56)  References Cited

U.S. PATENT DOCUMENTS

| | | | |
|---|---|---|---|
| 2007/0280412 A1* | 12/2007 | Defreitas ............. | A61B 6/0414 |
| | | | 378/37 |
| 2009/0213986 A1* | 8/2009 | Thaler .................. | A61B 6/0414 |
| | | | 378/208 |

\* cited by examiner

COMPRESSION DEVICE FOR BREAST EXAMS AND DIAGNOSTIC APPARATUS FOR BREAST EXAMS

This application is the National Phase of International Application PCT/IB2022/051145 filed Feb. 9, 2022 which designated the U.S.

This application claims priority to Italian Patent Application No. 102021000003593 filed Feb. 17, 2021, which applications are incorporated by reference herein.

The present invention relates to a compression device for examining a patient's breast as well as a diagnostic apparatus comprising said device.

More specifically, the present invention relates to a device for compressing and positioning the breast of a patient during examinations performed with image acquisition for the early detection of breast tumours.

Breast compression is a fundamental step in order to be able to conduct such examinations effectively.

In fact, in the field of optical imaging technology, compression blocks the circulation of the neoangiogenic vascular network created by the tumour, so that growth of deoxyhemoglobin is stimulated and detected by means of illumination with light at specific frequencies.

In addition, compression involves reducing the thickness of the patient's breast in order to ensure better detailing of the images resulting from the optical or radiographic examination (and to reduce the amount of electromagnetic waves needed, in the case of mammographic examinations).

It should also be noted that the image acquisition phase is improved by keeping the analysed area immobile. In this context, compression of the patient's breast is necessary for the file to block and immobilise the patient's breast in order to improve the quality of the images collected.

With regard to the optical analysis technique used, the patient's breast is illuminated with red light at 640 nm, while the light attenuation values detected by a camera, opposite the light source, correspond to changes in the concentration of deoxyhaemoglobin in the capillary vessels. This makes possible the detection of "neoangiogenesis" areas, i.e. areas of abnormal vascularisation generated to feed the tumour cells, regardless of the density of the tissue to be analysed.

As an example of application of this technique, the document U.S. Pat. No. 6,587,578 describes a Diffuse Optical Mammography system (DFOM) in which a breast supporting device is used and arranged between a fixed support and a flexible membrane which is part of a compression system. In particular, the membrane rests on the patient's breast and an external inflation system pushes the membrane into direct contact with the patient's breast providing it with a slight pressure. The device is cumbersome and complex to manage.

Moreover, the devices known in the art have important drawbacks in terms of adaptability to the shape of the breast. In fact, the compression devices (inflatable membranes) cannot adapt effectively to the size and morphology of the breasts.

In this context, the absence of an adjustment system leads to ineffectiveness in the compression actions with consequent disadvantages in the reliability of the diagnostic examination.

In addition, if the membrane is positioned incorrectly with respect to the patient's breast (for example too far in front of or too close to the sternum) the compression action is particularly painful.

The purpose of the present invention is therefore to provide a compression device for breast examinations and a diagnostic apparatus for breast examinations capable of resolving the aforementioned drawbacks.

In particular, a purpose of the present invention is to provide a compression device for breast exams that is extremely versatile and adaptable to the size and shape of the breast.

A further purpose of the present invention is to provide a compression device that is easy to apply, structurally simple, and able to compress the patient's breast effectively in order to optimise diagnostic activity for imaging.

Yet another purpose of the present invention is to provide a compression device which is able to compress uniformly the entire surface of the breast, and which is therefore particularly comfortable without causing pain to the patient.

A final purpose of the present invention is to provide a breast examination diagnostic apparatus comprising the compression device configured to be used with systems based on X-ray as well as optical technology, and compatible with the use of the ultrasound.

In accordance with the present invention, these and other purposes are achieved by a compression device for breast examinations comprising a support element defining a flat surface made at least in part of material transparent to light and configured to come into contact with a lower area of the breast; a substantially box-like body made at least in part of transparent material and comprising at least one elastic and deformable wall configured to compress an upper area of the breast, said elastic wall being opposite to the flat surface; and orientation means of the box-like body to move said body with respect to the support element and according to the size and shape of the breast.

These purposes are further achieved by a breast examination diagnostic apparatus comprising a pressurised fluid supply source; an illumination system; and an image acquisition device opposite said illumination system; characterised in that it comprises a compression device as described above.

Further features and advantages of the present invention are disclosed in the depending claims.

The characteristics and advantages of the present invention will become apparent from the following detailed description of a practical embodiment thereof, illustrated by way of example only in the accompanying drawings, in which.

With reference to the appended figures, a compression device for breast examinations in accordance with the present invention is collectively referred to as reference number 1. The device 1 is advantageously used in a breast diagnostic apparatus 100, also a subject matter of the present invention, schematically illustrated in FIGS. 3a and 3b.

Figure 1:
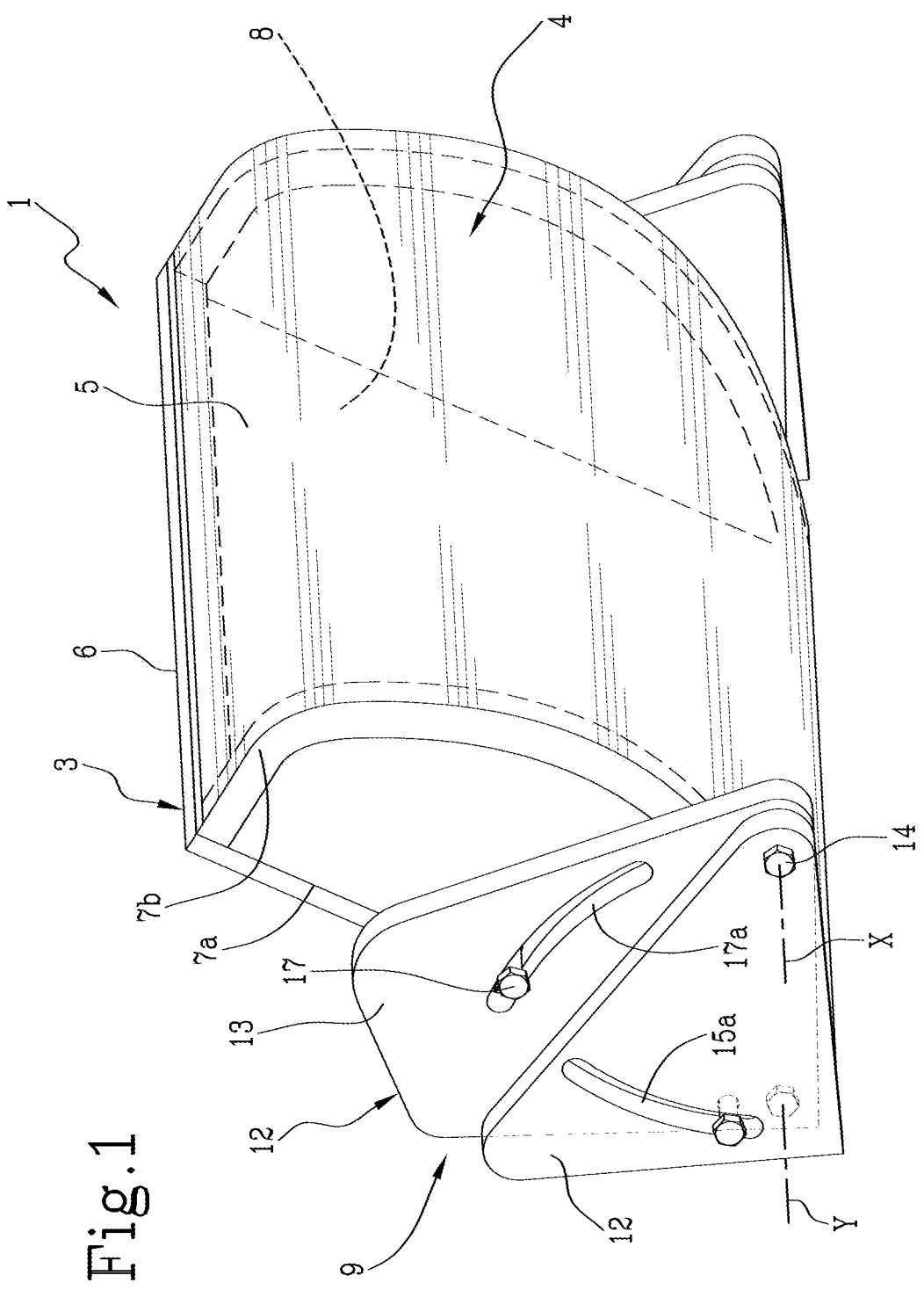
FIG. 1 shows a perspective view of a device for facilitating breast examination, in accordance with the present invention.
Figures 3A, 3B:
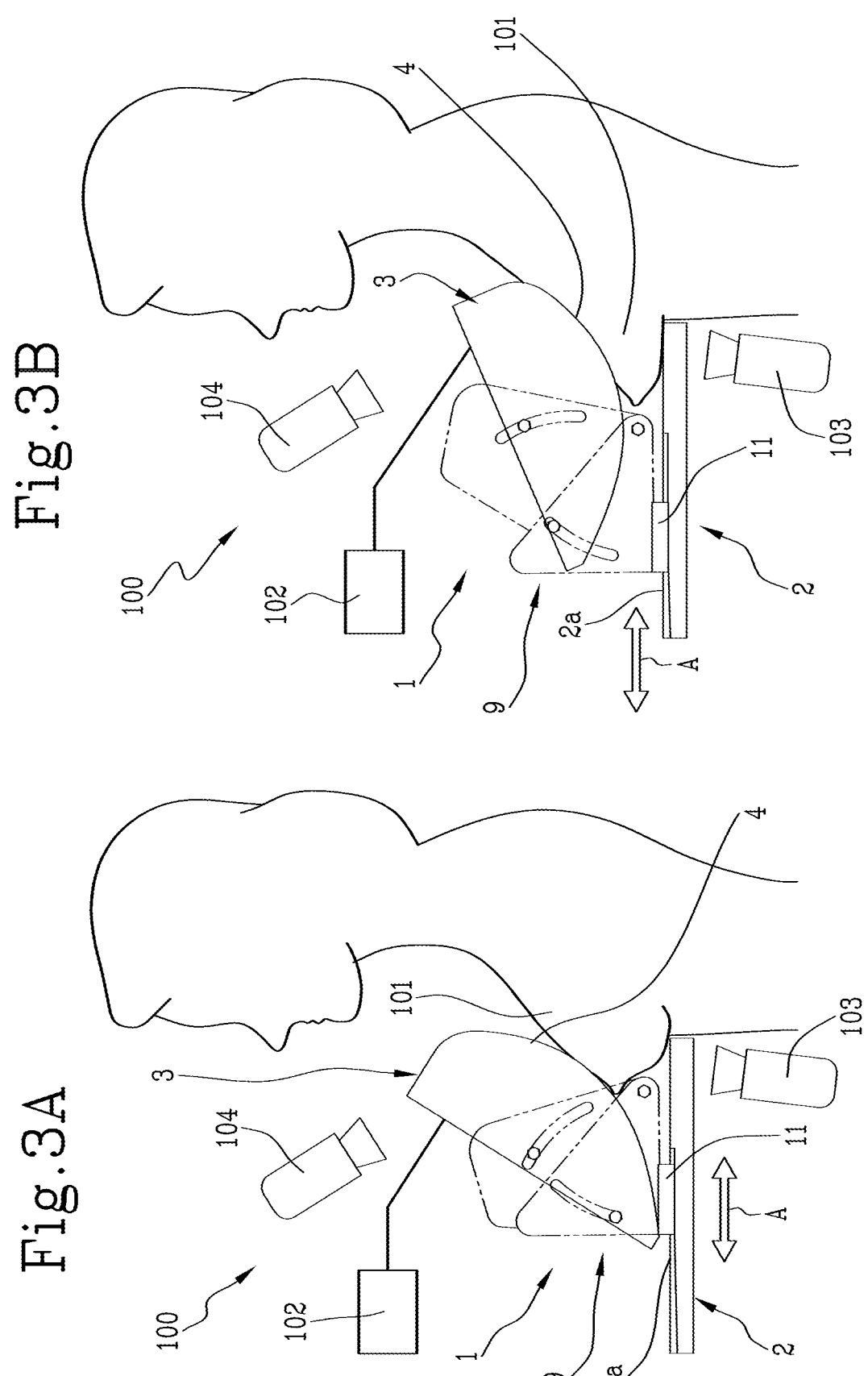
FIGS. 3a and 3b show the respective operating steps of a breast examination diagnostic apparatus according to the present invention and equipped with the compression device of FIG. 1.
Figure 4:
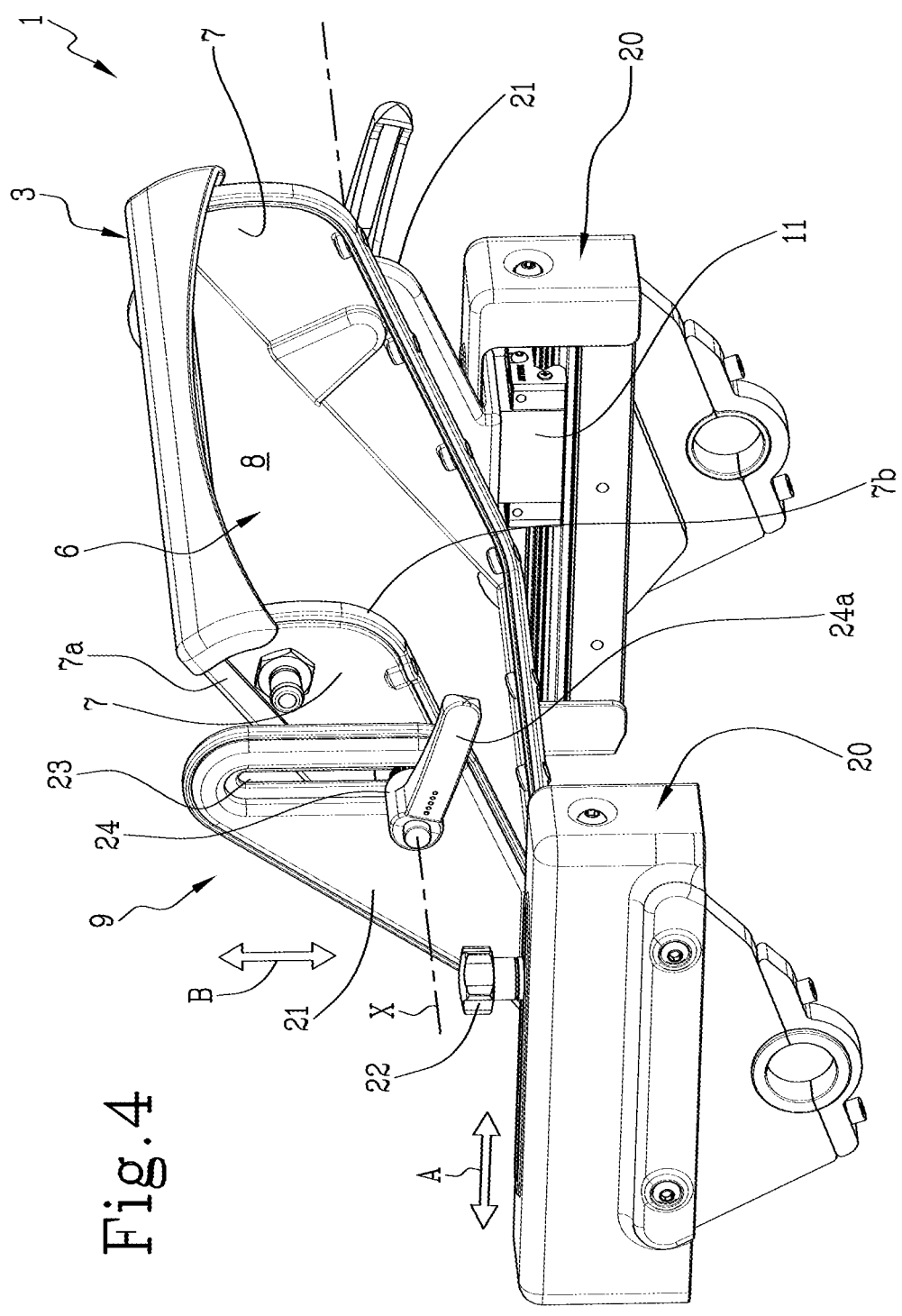
FIG. 4 shows a perspective view of the compression device for breast examinations in accordance with a second embodiment of the invention.

In particular, and as better illustrated in FIGS. 1 and 4, the compression device 1 comprises a support element 2 defining a flat surface 2a made at least in part of material transparent to light. The flat surface 2a is configured to come into contact with a lower area of the patient's breast 101. In fact, during use, the patient rests her breast 101 on the flat surface 2a as best illustrated in FIGS. 3a and 3b.

The device 1 further comprises a substantially box-like body 3 made at least in part of transparent material and comprising at least one elastic and deformable wall 4. Said elastic wall 4 is opposite the flat surface 2a and is advantageously configured to compress an upper area of the patient's breast 101. In this way, and referring again to FIGS. 3a and 3b, due to the compression action of the elastic wall 4 on the patient's breast 101, the latter is compressed against the flat surface 2a.

The device 1 also includes orientation means 9 of the box-like body 3 for moving the body 3 with respect to the support element 2, thus adapting the position of the elastic wall 4 to the size and shape of the patient's breast 101.

In other words, the orientation means 9 make it possible to move the entire box-like body 3 and orient it in order to support the elastic wall 4 adequately on the upper area of the patient's breast 101.

Advantageously, the elastic wall 4 comprises a transparent membrane 5 configured to be deformed under the action of an impression fluid.

Preferably, the membrane 5 is made of a soft material, impermeable to air and transparent to light radiation in the visible, infrared and X-ray spectra.

Furthermore, the membrane 5 is preferably made of a material that is not completely smooth so as to generate a friction force when in contact with the patient's breast 101.

With reference to the appended figures, the elastic wall 4 formed by the membrane 5 has an arcuate profile with convexity facing outwards from the body 3.

This ergonomic configuration, illustrated purely by way of example only, anatomically improves contact with the patient's breast 101 as well as the adhesion and retention actions of the patient's breast 101 during compression.

In this context, it should be recalled that the shape of the elastic wall 4, as well as the shape and dimensions of the entire box-like body 3, can be of any type, depending on the specific use.

Figure 2:
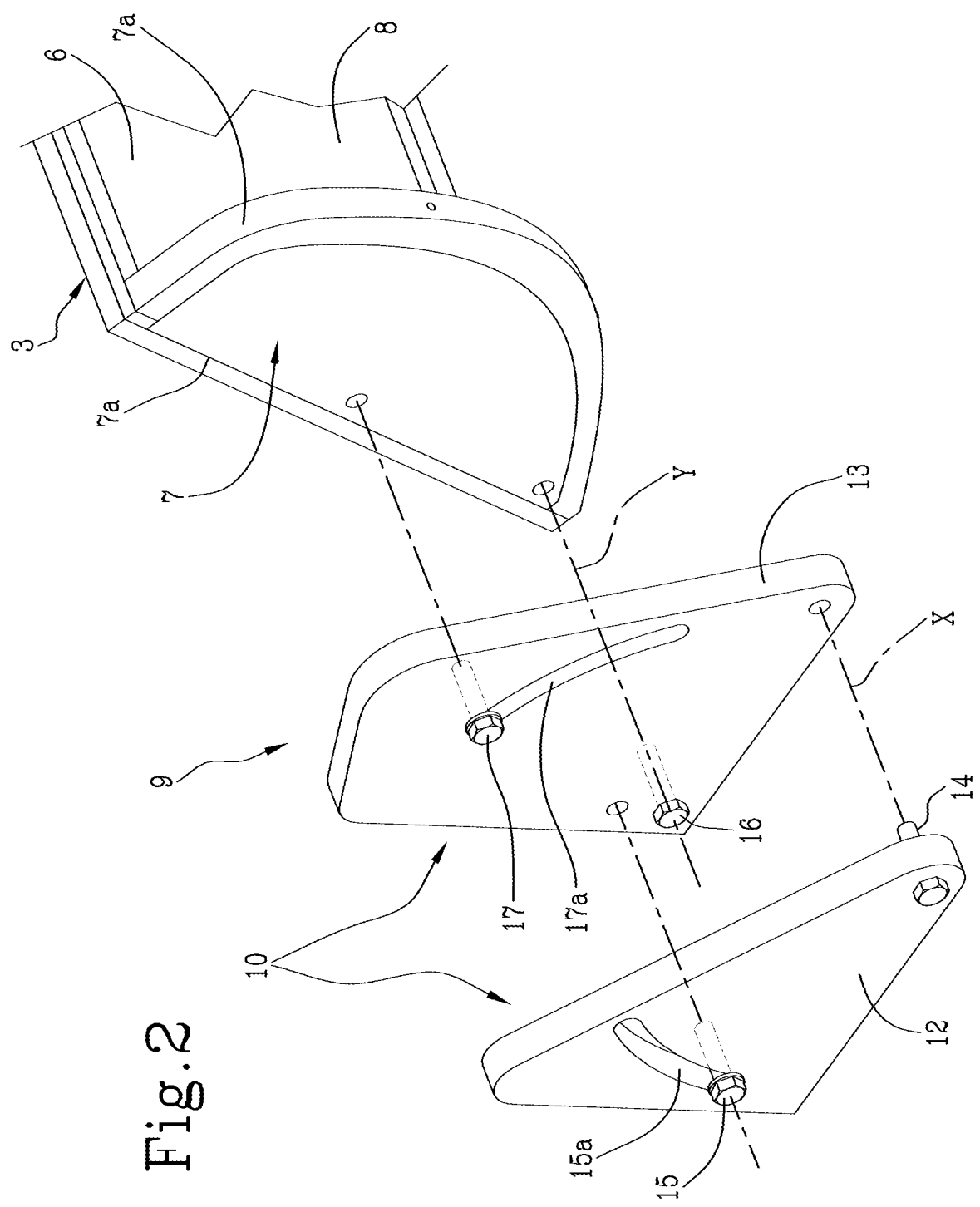
FIG. 2 shows an exploded and partial view of a construction detail of the device of FIG. 1.

Referring to FIGS. 1, 2 and 4, the box-like body 3 comprises a flat wall 6 opposite the membrane 5 made of rigid material and preferably transparent to light radiation in the visible, infrared and X-ray spectra. The flat wall 6 preferably has a rectangular profile in which the respective major sides are engaged at the edge of the membrane 5.

In this way, the flat wall 6 establishes a window that, in collaboration with the membrane 5, makes possible visual access to the patient's breast 101.

The box-like body 3 also comprises two side walls 7 made of a rigid material, each of which is interposed between the membrane 5 and the flat wall 6.

In greater detail, with reference to FIGS. 2 and 4, each side wall 7 has a substantially arcuate shape defining a straight side 7a associated with a respective smaller side of the flat wall 6 and an arcuate side 7b engaged with the edge of the membrane 5.

The box-like body 3 thus created has an internal chamber 8 between the flat wall 6, the membrane 5 and the two side walls 7.

Chamber 8 is configured to be in fluid communication with a supply source 102 (FIGS. 3a and 3b) of a pressurised fluid. Advantageously, the pressurised fluid (preferably air) is fed inside the chamber 8 to dilate the membrane 5 and deform it outwards in order to perform a compressing action on the patient's breast 101 (FIG. 3b).

As described above, the box-like body 3 is moved so as to position the membrane 5 correctly on the patient's breast

101 by the action of orientation means 9 that support the body 3 above the flat surface 2a.

In accordance with a first embodiment of the invention better illustrated in FIGS. 1 and 2, the means 9 comprise at least one connecting portion 10 hinged to a respective side wall 7 and sliding on the support element.

Preferably, a pair of connecting portions 10 is provided in which each portion 10 is hinged to a respective side wall 7. Furthermore, each portion 10 comprises a skid 11 (schematically shown in FIGS. 3a and e3b) for sliding on the flat surface 2a along a direction A away from/approaching the patient's body.

For this purpose, respective slide guides for the skids 11 are provided on the edges of the support element 2.

With particular reference to FIG. 2, it should be noted that each connection portion 10 consists of a first element 12 integral with the respective skid 11, and a second element 13 hinged to the respective side wall 3.

The first element 12 is made in the form of a plate having a triangular profile in which a base side defining a cathetus is engaged to the skid 11 and an oblique side defining the hypotenuse is directed towards the patient. Note that during the movement along direction A, the first element 12 does not vary in its orientation.

The second member 13 is in the form of a plate having a rectangular trapezium profile. However, it should be specified that the elements can have any configuration according to their specific use and the overall dimensions of the device 1.

The second element 13 is rotatably associated with the first member 12 to rotate relative to the first member 12 around a respective first X axis perpendicular to the sliding direction A of the skid 11.

To this end, the elements 12 and 13 are reciprocally pivoted at ends close to the patient's body (coincident angles of the two elements 12 and 13) by a first pivot 14 which extends along the X axis.

In addition, the second element 13 has a second pin 15 inserted into a first arcuate cavity 15a obtained in the first element 12. In this way, the second element 13 rotates around the first pin 14 by sliding the second pin 15 inside the respective first arcuate cavity 15a.

Furthermore, the box-like body 3 is rotatably associated with the second element 13 to rotate with respect to the second element 13 around a respective second Y axis parallel to the first X axis and perpendicular to the sliding direction A of the skid 11.

In particular, with reference to FIG. 2, the second member 13 and the respective side wall 7 are connected at a distal end of the patient's body by a third pin 16.

In this case, too, the side wall 7 also has a fourth pin 17 insertable into a second arcuate cavity 17a obtained in the second element 13.

Advantageously, in this configuration the box-like body 3 rotates around the third pin 16, extending longitudinally along the Y axis, to slide the fourth pin 17 along the second arcuate cavity 17a.

In this situation, it should be noted that the device 1 makes broad mobility possible for the box-like body 3 that supports the membrane 5.

This mobility, defined by a plurality of degrees of freedom of the body 3, makes it possible to bring the membrane 5 closer to/away from the patient's breast 101 by means of sliding along the direction A. At the same time, it is possible to raise/lower the membrane 5 with respect to the patient's breast 101 by rotating the second element 13 with respect to the first element 12 around the X axis.

Again, it is possible to tilt the body 3 by rotating it with respect to the second element 13 around the Y axis. This latter movement makes it possible for the membrane 5 to be positioned by adapting its orientation to the shape of the patient's breast 101.

In accordance with a second embodiment of the present invention illustrated in FIG. 4, the skids 11 are slidable along the direction A within appropriate support bars 20.

The bars 20 are in turn supported by a support frame known in the art, hence not disclosed or illustrated herein.

Each bar 20 also has a clamping screw 22, suitably shaped to be grasped by the operator and which allows the body 3 to be locked in position along the direction A. In greater detail, the clamping screw is inserted within a slot formed in the bar 20. In this way, the screw slides into the slot by moving the body 3 along the direction A. Once the correct position has been found, the screw 22 is tightened to lock the body 3 in place with respect to the patient's breast 101.

Inside the bars 20 is the flat surface 2a, not shown in FIG. 4 so as to give greater visibility to other parts of the device 1.

Furthermore, the membrane 5 of the body 3 is also not illustrated in FIG. 4 so as to give greater visibility to the interior of the chamber 8 and the wall 6.

In this embodiment, the orientation means 9 comprise a pair of flanges 21 each of which is associated with a respective skid 11.

Each flange 21 has a slot 23 which is vertical and therefore transversal to the direction A.

In this situation, the body 3 is engaged on opposite sides of the flanges 21 by means of suitable rotation pins 24 passing through the respective slots 23.

In particular, each pin 24 extends from a respective side wall 7 and through the slot 23.

In this way, the body 3 is rotatable around the X axis defined by the longitudinal development of the pin 24. In addition, the body 3 slides in a height-adjustable way along the direction B, which is to say towards/away from the surface 2a. The slide along the direction B is achieved by sliding the pins 24 along the respective slots 23.

In addition, each pin has a locking handle 24a protruding outwards from the slot 23 which makes it possible to lock the position of the pin 24 with respect to the slot, constraining the body 3 in a preset position with respect to the flanges 21.

In other words, by acting on the handles 24a screwed onto the pins 24, it is possible to release the body 3, rotate it around the X axis and raise/lower it along the direction B according to the position and size of the patient's breast 101. Once the body 3 has been positioned, screwing the handles 24a permanently constrains the body 3 in the set position.

The device 1 described above is advantageously used in a breast examination diagnostic apparatus 100 which is also part of the present invention.

The apparatus 100, schematically illustrated in FIGS. 3a and 3b, comprises a supply source 102 of a pressurised fluid, preferably air, in fluid communication with the chamber 8 of the box-like body 3. For this purpose, supply ducts are provided to distribute the pressurised fluid within the chamber 8 by expanding the membrane 5 on the breast.

In other words, the excess pressure inside the chamber 8 deforms the membrane 5 outwardly, causing the patient's breast 101 to be compressed against the flat surface 2a.

The supply source 102 also makes it possible for the fluid (air/gas) to be introduced into the chamber 8 with transient trends configurable according to the acquisition and processing of the diagnostic images.

In addition, the supply source 102, in addition to allowing adjustment of the pressure to be reached in the chamber 8, makes possible the stabilisation of the set pressure, keeping it unchanged throughout the duration of the examination, and compensating for the patient's micro-movements (such as those due to breathing).

The apparatus 100 further comprises an illumination system 103 arranged at the support element 2 on the opposite side of the patient's breast 101. In particular, the illumination system 103 is placed below the support element 2 to direct a light beam towards the lower area of the breast.

In this context, it should be noted that the transparent material with which the flat surface 2a is made allows the passage of light towards the patient's breast 101.

Furthermore, the apparatus 100 comprises an image acquisition device 104 opposite the illumination system 103.

In greater detail, the image acquisition device 104 is arranged at the flat wall 6 on the opposite side of the patient's breast 101, in such a way as to acquire the images through the transparent "window" defined by the wall 6 and the membrane 5.

In accordance with the present invention, the image acquisition device 104 may be of any suitable type in order to perform a breast 101 diagnostic examination.

For example, the image acquisition device 104 may consist of an optical camera or radiographic apparatus.

Finally, the apparatus 100 comprises the device 1 described above, configured to compress the patient's breast to facilitate and foster the acquisition of the diagnostic images.

In practice, the patient's breast 101 is then placed on the flat surface 2a.

In this situation, the patient is placed with her mammary cleft flush with the outer edge of surface 2a.

Thereafter, the device 1 is approached using the associated degrees of freedom, so that the membrane 5 is partially in contact with the patient's breast 101 which is completely under the membrane 5.

In other words, the body 3 is moved along the direction A and around the X and Y axes.

Once the appropriate position has been found, the device 1 is constrained (by means of locking systems, known in the art and hence not disclosed here) to proceed with the examination.

The supply source 102 is then activated to introduce the pressurised fluid into the chamber 8 of the body 3.

As a result, the membrane 5 is dilated against the patient's breast 101. In this way, by increasing in volume the membrane 5 settles gradually into position and progressively compresses the patient's breast 101 towards the chest and then towards the flat surface 2a, causing it to stretch.

A servo valve (not disclosed or illustrated herein, as it is copyleft) of the supply source 102 checks that the desired pressure, and consequent deformation, is reached and maintained, even when faced with small movements such as breathing.

Adhesion of the membrane 5 to the patient's breast 101 also produces, by means of friction, an immobilising effect so that it is difficult, although not impossible, for the patient to move.

In this way, the image acquisition device 104 that provides the diagnosis on the patient's breast 101 is activated.

Advantageously, the device 1 ensures a comfortable and complete immobilisation of the organ and makes execution of a reliable examination possible.

Furthermore, the pressure exerted by the membrane 5 on the patient's breast 101 results in a momentary block of the microcirculation in the capillaries with consequent formation of deoxyhemoglobin. The phenomenon is more relevant in neoangiogenic capillaries than in healthy capillaries, due to their lower elasticity and the lower pressure required to obstruct them, which implies a higher concentration of deoxyhemoglobin and longer oxygenation recovery times. Therefore, important information is provided on the presence of a possible network of vessels dedicated to feeding a nascent tumour.

It is therefore possible to detect the tumour by seeking the network of vessels feeding it, neoangiogenesis, which is much more extensive and identifiable than the tumour itself.

Advantageously, the device 1 is compatible with devices that use different diagnostic methods (optical and/or X-ray), and facilitates integration of the same with the ultrasound methodology.

Furthermore, the device 1 is particularly easy to use, is not overly expensive and is simple in structure, all this while making efficient and controllable compression possible at all stages of the examination.

In addition, with its different degrees of adjustment, the device 1 is adaptable to the patient's breast 101 and torso. Accordingly, the entire compression action is painless and more comfortable than the compression systems known in the art.

Finally, the device 1 is compatible with the use of ultrasound scanners that make it possible to access the patient's breast 101 directly with the ultrasound probe at the end of the optical examination, leaving it positioned on the upper surface 2a.

The invention claimed is:

1. A compression device for breast exams, comprising:
a support element defining a flat surface made at least in part of material transparent to light and configured to come into contact with a lower area of a breast;
a substantially box shaped body made at least in part of transparent material and comprising at least one elastic and deformable elastic wall configured to compress an upper area of the breast, said elastic wall being opposite the flat surface and comprising a membrane configured to be deformed under action of a pressurized fluid; and
an orientation device for moving the box shaped body with respect to the support element and as a function of the dimensions and shape of the breast;
wherein said box shaped body comprises: a flat wall opposite said membrane and made of rigid and transparent material, and two side walls made of rigid material and each of which is interposed between the membrane and the flat wall;
wherein said orientation device comprises a pair of connection portions each hinged to a respective one of the side walls;
each of the connection portions further comprising a respective skid for sliding on the flat surface along a sliding direction away from/approaching a patient's body as a function of the dimensions of the breast.

2. The compression device according to claim 1, wherein said box shaped body internally comprises a chamber defined between said flat wall, said membrane, and said side walls; said chamber being configured to be in fluid communication with a supply source of the pressurized fluid.

3. The compression device according to claim 1, wherein each of the connection portions comprises a first element integral with the respective skid, and a second element hinged to the respective one of the side walls; said second element being rotatably connected to said first element to rotate with respect to the first element and around a respective first axis perpendicular to the sliding direction of the respective skid.

4. The compression device according to claim 3, wherein each element is made in the form of a plate; said first and second element being connected at an end near the patient's body by a first pin; said second element further including a second pin inserted in a first arcuate cavity obtained in the first element; said second element rotatable around the first pin to slide the second pin in said first arcuate cavity.

5. The compression device according to claim 3, wherein said box shaped body is rotatably connected to said second element to rotate with respect to the second element and around a respective second axis parallel to the first axis and perpendicular to the sliding direction of the respective skid.

6. The compression device according to claim 5, wherein said second element and the respective one of the side walls are connected at a distal end from the patient's body by a third pin; said respective one of the side walls further including a fourth pin insertable in a second arcuate cavity in the second element; said box shaped body rotatable around the third pin to slide the fourth pin in said second arcuate cavity.

7. A compression device for breast exams, comprising:
a support element defining a flat surface made at least in part of material transparent to light and configured to come into contact with a lower area of a breast;
a substantially box shaped body made at least in part of transparent material and comprising at least one elastic and deformable elastic wall configured to compress an upper area of the breast, said elastic wall being opposite the flat surface and comprising a membrane configured to be deformed under action of a pressurized fluid; and
an orientation device for moving the box shaped body with respect to the support element and as a function of dimensions and shape of the breast;
wherein said box shaped body comprises: a flat wall opposite said membrane and made of rigid and transparent material, and two side walls made of rigid material and each of which is interposed between the membrane and the flat wall;
wherein said orientation device further comprises at least one pair of flanges each hinged to respective ones of the side walls and slidably engaging respective bars arranged on opposite sides of the flat surface.

8. The compression device according to claim 7, wherein each of the flanges comprises the respective skid for sliding on the bar along the sliding direction.

9. The compression device according to claim 8, and further comprising a pair of pins each of which protrudes from the respective one of the side walls and extends inside a respective slot in the flange.

10. The compression device according to claim 9, wherein the box shaped body is rotatable around a pin axis defined by a longitudinal extension of the pins and is slidable along a direction defined by the slots approaching/away from the flat surface.

11. The compression device according to claim 9, wherein said flat wall and said membrane are made of material transparent to light radiations in the visible, infrared and X-ray spectrum.

12. A diagnostic apparatus for breast examinations, comprising:
the compression device in accordance with claim 1;
a supply source of the pressurized fluid;
an illumination system; and an image acquisition device opposite said illumination system.

13. The diagnostic apparatus according claim 12, wherein said illumination system is arranged at the support element on an opposite side of the breast to direct a light beam towards the breast and through the flat surface.

14. The diagnostic apparatus according to claim 12, wherein said box shaped body internally comprises a chamber defined between said flat wall, said membrane, and said side walls; said chamber being configured to be in fluid communication with the supply source of the pressurized fluid for distributing the pressurized fluid in the chamber and dilating the membrane on the breast.

15. The diagnostic apparatus according to claim 12, wherein said image acquisition device is arranged at the flat wall on an opposite side of the breast to acquire images through the flat wall and the membrane.

16. The diagnostic apparatus according to claim 15, wherein said image acquisition device comprises an optical and/or radiographic camera and/or an ultrasound.

17. A diagnostic apparatus for breast examinations, comprising:

a compression device for breast exams, comprising:

a support element defining a flat surface made at least in part of material transparent to light and configured to come into contact with a lower area of a breast;

a substantially box shaped body made at least in part of transparent material and comprising at least one elastic and deformable elastic wall configured to compress an upper area of the breast, said elastic wall being opposite the flat surface and comprising a membrane configured to be deformed under action of a pressurized fluid; and an orientation device for moving the box shaped body with respect to the support element and as a function of dimensions and shape of the breast;

wherein said box shaped body comprises: a flat wall opposite said membrane and made of rigid and transparent material, and two side walls made of rigid material and each of which is interposed between the membrane and the flat wall;

wherein said orientation device comprises a pair of connection portions each hinged to a respective one of the side walls;

a supply source of the pressurized fluid;

an illumination system; and an image acquisition device opposite said illumination system.

18. The diagnostic apparatus according claim 17, wherein said illumination system is arranged at the support element on an opposite side of the breast to direct a light beam towards the breast and through the flat surface.

19. The diagnostic apparatus according to claim 17, wherein said box shaped body internally comprises a chamber defined between said flat wall, said membrane, and said side walls; said chamber being configured to be in fluid communication with the supply source of the pressurized fluid for distributing the pressurized fluid in the chamber and dilating the membrane on the breast.

20. The diagnostic apparatus according to claim 15, wherein said image acquisition device comprises an optical and/or radiographic camera and/or an ultrasound.

* * * * *